United States Patent [19]

Irani

[11] 4,032,584

[45] June 28, 1977

[54] STABILIZED METHYLENE CHLORIDE

[75] Inventor: Mazin R. Irani, Tarrytown, N.Y.

[73] Assignee: Stauffer Chemical Company, Westport, Conn.

[22] Filed: May 3, 1976

[21] Appl. No.: 682,284

[52] U.S. Cl. .......................... 260/652.5 R; 134/40
[51] Int. Cl.² ........................................ C07C 17/42
[58] Field of Search ............... 260/652.5 R; 134/40

[56] References Cited

UNITED STATES PATENTS

| | | | |
|---|---|---|---|
| 1,904,450 | 4/1933 | Harris | 260/652.5 R |
| 3,887,628 | 6/1975 | Beckers | 260/652.5 R |
| 3,989,640 | 11/1976 | Culver | 260/652.5 X |

Primary Examiner—Delbert E. Gantz
Assistant Examiner—J. Thierstein
Attorney, Agent, or Firm—Charles B. Rodman

[57] ABSTRACT

A stabilized methylene chloride composition consisting essentially of methylene chloride and stabilizing amounts of mixed amylenes, propylene oxide, butylene oxide and tertiary butylamine.

3 Claims, No Drawings

STABILIZED METHYLENE CHLORIDE

BACKGROUND OF THE INVENTION

This invention relates to the stabilization of methylene chloride, and more particularly, it relates to the stabilization of methylene chloride against degradation when exposed to heat, light and air.

Methylene chloride ($CH_2Cl_2$, boiling point 40.1° C.) is a highly versatile and useful solvent for various industrial applications at both normal and elevated temperatures. It is the least toxic of the chloromethanes. Its outstanding solvent properties are the principal basis of its industrial interest. A particularly important industrial use of methylene chloride is in the vapor degreasing of metals.

Among the properties which make methylene chloride so attractive in degreasing applications is its greater stability than other chlorinated hydrocarbon solvents such as perchloroethylene, trichloroethylene and methyl chloroform. For example, methylene chloride is more resistant to oxidation, hydrolysis and pyrolysis than other chlorinated solvents. Additionally, methylene chloride can be used to greater advantage than other degreasing solvents in vapor degreasing metals, since it can be used effectively at lower temperatures due to its lower boiling point and excellent stability. Methylene chloride is particularly desirable for degreasing since it is substantially resistant to photochemical activity and, therefore, does not contribute to air pollution by smog formation.

Methylene chloride does have disadvantages when used in certain metal cleaning functions, including vapor degreasing. For example, methylene chloride can react with aromatic and aliphatic compounds in the presence of metals, metal halides and combinations thereof, including aluminum, zinc and iron, halides thereof, and combinations of said metals and halides. The reaction product is generally an objectionable high boiling tarry substance which renders the methylene chloride unsuitable for further use.

Compounds that react with methylene chloride to produce tarry substances are generally introduced into the methylene chloride from various cutting oils and lubricants used in metal fabricating operations, which are carried over into the methylene chloride solvent during vapor degreasing or other cleaning of the fabricated metal parts. Solvent manufacturing, handling and storage equipment are other sources which can introduce these impurities.

Minor quantities of various organic compounds have been incorporated into methylene chloride to prevent degradation and other types of deterioration such as oxidation, hydrolysis and pyrolysis. These organic compounds act as stabilizers to substantially prevent degradation of methylene chloride and to inhibit reactions which can lead to decomposition and corrosion.

In recent years, neutral stabilizing systems for methylene chloride have been found to be particularly advantageous. These systems generally contain as a principal component, an essentially neutral compound which acts as an acceptor of strong acids such as hydrochloric acid, but does not ordinarily react with weak organic acids. This neutral compound is generally an epoxide such as butylene oxide, propylene oxide, epichlorohydrin, butadiene dioxide, styrene oxide, glycidol, pentene oxide, cyclohexene oxide, or a mixture of two or more of these.

Many additives have been suggested as stabilizers for methylene chloride, nevertheless, there is still a great need for improving the stability of $CH_2Cl_2$ at high temperatures. When methylene chloride is stabilized, its tendency towards reaction is diminished. However, during the course of high temperature applications, stabilizers have a tendency to degrade, thereby increasing the tendency of methylene chloride to react. This situation has made the stabilization of methylene chloride over long periods of time, e.g. two to three weeks, at high temperature very difficult.

It has, therefore, been an arduous and empirical task for practitioners in the art to develop a suitable stabilizing formulation for methylene chloride which extends the period of stabilization at high temperatures. The present invention has achieved an efficient and commercially economical stabilizer package for methylene chloride which enables the use of methylene chloride at high temperatures over long periods of time.

DESCRIPTION OF THE PREFERRED EMBODIMENT

In accordance with the present invention, methylene chloride has been stabilized for use as a vapor degreasing solvent for long periods of time at high temperatures with a stabilization package comprising mixed amylenes, propylene oxide, butylene oxide and tertiary butylamine. This particular stabilizing package has maintained the stability of methylene chloride for as long as five weeks at reflux temperatures and vapor degreasing conditions.

The quantity of the stabilizing agents useful in the practice of the present invention will vary depending upon the conditions of use, however, all components must be used to achieve the desired results.

The stabilized $CH_2Cl_2$ composition of the present invention can be used for degreasing metals by contacting the metals with the composition. Thus, the process for vapor degreasing metals comprises contacting the metals to be degreased with methylene chloride vapor containing stabilizing amounts of mixed amylenes, propylene oxide, butylene oxide and tertiary butylamine.

The quantity of mixed amylenes can generally vary within the range of from about 0.01% to about 2.5% and preferably from about 0.10 to about 1.5% by weight of the methylene chloride. The mixed amylenes can generally contain mixtures of 2-methyl-2-butene, 2-methyl-1-butene and 3-methyl-1-butene in all combinations, and small amounts of pentanes which are generally formed during manufacture of the mixed amylenes.

Propylene oxide is generally used within a range of from about 0.01% to about 2.0% and preferably from about 0.05% to about 0.75% by weight of the methylene chloride. Butylene oxide is generally used within the range of from about 0.01% to about 0.75% and preferably from about 0.05% to about 0.75% by weight of the methylene chloride. Tertiary butylamine is generally used within the range of from about 1 ppm to about 0.01% and preferably from about 1 ppm to about 50 ppm by weight of the methylene chloride. Although higher concentrations of the above can be used, if desired, no additional benefit is obtained in the way of increased stabilization and the cost of the stabilization package is unnecessarily increased.

In several laboratory tests a coupon of aluminum was contacted with methylene chloride containing different stabilizer packages. These tests were carried out in different environments. In the examples which follow, all parts and percentages are by weight unless otherwise indicated.

In examples I through V, it was observed that when the pH dropped below 5, the aluminum started to corrode. When the pH dropped below 4, the precipitate started to form and in some instances the solvent turned yellow.

EXMPLE I

In this example, a coupon of aluminum was suspended over methylene chloride at a refluxing temperature of 40° C. for a period of 48 hours. Different additive packages were employed. The pH of the $CH_2Cl_2$ was measured at the beginning of the test and after a 48 hour period. A commerical stabilizing package was used as a control. It had the following analysis:

| Constituent | Wt. % |
|---|---|
| 2-methyl butene-2 | 0.5 |
| Propylene oxide | 0.2 |
| Butylene oxide | 0.07 |
| Isoprene | 0.03 |
| Isopentane | 0.01 |

-continued

| Constituent | Wt. % |
|---|---|
| Cyclohexane | 0.01 |

The results are listed below in Table I.

TABLE I pH of $CH_2Cl_2$ Mixtures - Reflux Temperature (40° C. ±)

| Additive Level | | | | pH at | |
|---|---|---|---|---|---|
| % Mixed Amylenes | % Propylene Oxide | % Butylene Oxide | % Tertiary Butyl Amine | 0 hours | 48 hours |
| CONTROL | | | | 8.4 | 8.2 |
| 0.5 | 0.3 | 0.1 | 0.001 | 8.4 | 8.0 |
| — | — | — | 0.001 | 7.1 | 7.4 |
| 0.5 | — | 0.1 | — | 6.4 | 6.3 |
| — | 0.5 | — | 0.001 | 7.0 | 6.1 |
| — | 1.0 | — | — | 5.3 | 5.7 |
| — | — | 0.5 | — | 6.5 | 5.5 |
| 1.0 | — | — | — | 5.7 | 5.3 |
| — | — | — | — | 5.2 | 5.2 |
| 0.5 | 0.3 | 0.1 | — | 4.8 | 4.4 |
| — | 0.5 | 0.5 | — | 5.1 | 4.1 |
| 0.5 | 0.3 | — | — | 5.3 | 4.1 |

EXAMPLE II

A coupon of aluminum was suspended over methylene chloride containing 1% toluene and 10 parts per million of $AlCl_3$ at a refluxing temperature of 40° C. for 48 hours. A variety of stabilization packages were used including the control of Example 1. Table II lists pH obtained at the beginning of the run and 48 hours.

TABLE II pH of $CH_2Cl_2$ Mixtures (1% Toluene and 10 ppm $AlCl_3$ Added) at Reflux Temperature (40° C. ± 1)

| Additive Level | | | | pH at | |
|---|---|---|---|---|---|
| % Mixed Amylenes | % Propylene Oxide | % Butylene Oxide | Tertiary Butyl Amine | 0 hours | 48 hours |
| 0.5 | 0.3 | 0.1 | 0.001 | 8.1 | 8.3 |
| CONTROL | | | | 8.1 | 8.1 |
| — | — | 0.5 | — | 5.4 | 6.1 |
| — | 1.0 | — | — | 5.0 | 5.5 |
| 1.0 | — | — | — | 4.3 | 5.1 |
| — | 0.5 | 0.5 | — | 5.5 | 4.7 |
| 0.5 | 0.3 | 0.1 | — | 4.8 | 4.5 |
| — | — | — | — | 8.5 | 1.5 |
| — | — | — | 0.001 | 7.5 | <1 |

EXAMPLE III

A coupon of aluminum was submerged in methylene chloride at a temperature of approximately 24° C. pH measurements were taken at the beginning of the test and at the end of a 48 hour exposure period. A variety of stabilizing packages were employed, including the control of Example I. The data appears below in Table III.

TABLE III pH of $CH_2Cl_2$ Mixtures - Room Temperature (24° C. ±)

| Additive Level | | | | pH at | |
|---|---|---|---|---|---|
| % Mixed Amylenes | % Propylene Oxide | % Butylene Oxide | % Tertiary Butyl Amine | 0 Hours | 48 Hours |
| CONTROL | | | | 8.4 | 8.2 |
| 0.5 | 0.3 | 0.1 | 0.001 | 8.4 | 8.0 |
| — | — | — | 0.001 | 7.8 | 7.7 |
| — | 0.5 | — | 0.001 | 7.2 | 7.0 |
| — | — | 0.5 | — | 6.5 | 6.2 |
| — | 0.5 | 0.5 | — | 5.1 | 6.0 |
| — | — | — | — | 5.2 | 5.4 |
| 0.5 | 0.3 | 0.1 | — | 4.8 | 5.3 |
| — | 1.0 | — | — | 5.3 | 4.9 |
| 0.5 | 0.3 | — | — | 5.3 | 4.8 |
| 1.0 | — | — | — | 5.7 | 4.7 |
| 0.5 | — | 0.1 | — | 6.4 | 4.6 |

EXAMPLE IV

A coupon of aluminum was submerged in methylene chloride at a temperature of 24° C. The methylene chloride contained 1% toluene and 10 ppm of aluminum chloride. The pH was measured at the beginning of the test and after 48 hours. A variety of stabilizing additives were used including the control of Example I. The data appears in Table IV below.

TABLE IV pH of $CH_2Cl_2$ Mixtures (1% Toluene and 10 ppm $AlCl_3$ Added) at Room Temperature (24° C. ± 1)

| % Mixed Amylenes | % Propylene Oxide | % Butylene Oxide | % Tertiary Butyl Amine | pH at 0 Hours | pH at 48 Hours |
|---|---|---|---|---|---|
| — | — | 0.5 | — | 5.4 | 6.2 |
| 0.5 | 0.3 | 0.1 | 0.001 | 8.1 | 5.6 |
| — | 1.0 | — | — | 5.0 | 5.5 |
| — | 0.5 | 0.5 | — | 5.5 | 5.0 |
| 0.5 | 0.3 | 0.1 | — | 4.8 | 4.1 |
| CONTROL | | | | 8.1 | 3.5 |
| — | — | — | — | 8.5 | 3.5 |
| 1.0 | — | — | — | 4.3 | 1.5 |

EXAMPLE V

A long range stability study was conducted wherein a coupon of aluminum was suspended over methylene chloride refluxed at a temperature of 40° C. for a period extending almost 2½ weeks. Four different stabilizer formulations were used. These are tabulated below in Table V. The pH data obtained from this study is recorded below in Table VI. It should be noted that for all formulations, no makeup solvent was added during the test.

TABLE V

| Stabilizer 1 | | Stabilizer 2 | |
|---|---|---|---|
| Constituent | Wt. % | Constituent | Wt. % |
| Mixed amylenes | 0.5 | 2-methylbutene-2 | 0.5 |
| Propylene oxide | 0.3 | Propylene oxide | 0.2 |
| Butylene oxide | 0.1 | Butylene oxide | 0.07 |
| Tertiary butyl amine | 10 ppm | Isoprene | 0.03 |
| | | Isopentane | 0.01 |
| | | Cyclohexane | 0.01 |

| Stabilizer 3 | |
|---|---|
| Constituent | Wt. % |
| Mixed amylenes | 1.5 |
| Propylene oxide | 0.9 |
| Butylene oxide | 0.3 |
| Tertiary butyl amine | 30 ppm |

TABLE VI

| Time (in hours) | Stabilizer 1 | Stabilizer 2 | Stabilizer 3 |
|---|---|---|---|
| 0 | 8.20 | 8.20 | 9.15 |
| 19 | 7.70 | 7.65 | — |
| 26 | 7.30 | 7.80 | — |
| 43 | 7.95 | 7.95 | — |
| 50 | 7.60 | 7.95 | — |
| 67 | 7.40 | 7.80 | 9.20 |
| 139 | 7.45 | 7.65 | 9.15 |
| 163 | 7.25 | 7.65 | — |
| 170 | 7.65 | 7.80 | 9.15 |
| 187 | 6.85 | 7.60 | — |
| 194 | 7.75 | 7.80 | 9.15 |
| 218 | 7.85 | 7.45 | — |
| 235 | 7.90 | 8.10 | 9.15 |
| 242 | 7.85 | 7.80 | 9.15 |
| 355 | 7.60 | 7.90 | 9.15 |
| 362 | 7.75 | 7.50 | — |
| 386 | 7.65 | 7.75 | — |
| Δ pH = | 0.55 | 0.45 | 0 |

EXAMPLE 6

In an extended test, two commercial vapor degreasers were used to evaluate the stability of a methylene chloride stabilizer package having the following additives, expressed as weight percent of methylene chloride:

0.48% mixed amylenes
0.10% butylene oxide
0.30% propylene oxide
8 parts per million tertiary butylamine The first commercial degreaser (hereafter referred to as "degreaser A") was cylindrical in shape and had a capacity of about 40 gallons of solvent. It was used to remove quench oil from steel parts. The second commercial degreaser (hereafter referred to as "degreaser B") was rectangular in shape and had a capacity of about 55 gallons of solvent. Its primary use was to remove working fluids from machined parts made from steel and aluminum. In the operation of either degreaser, a stream of condensed methylene chloride vapors was collected in a trough below the cooling coils and periodically directed at the parts to be degreased. It was important, therefore, to determine any degradation occurring not only in the refluxing solvent, but also in the vapor condensate. Thus, samples of both the boiling solvent (hereafter referred to as "liquid") and the vapor condensate (hereafter referred to as "condensate") were taken every 24 hours from both degreasers for a period of four weeks. Each sample was analyzed for acid acceptance by ASTM method number D2942-74. In addition, the additive levels, moisture content, non-volatile matter (NVM) after filtration, and the pH of the liquid were determined. The condensate was also analyzed for its additive levels, except for tertiary butyl amine. This data is reported below in Tables I and II. It is to be noted that 35 gallons of solvent were used in degreaser A and 55 gallons were used in degreaser B. Ten gallons were used as a makeup solvent in degreaser A. No makeup solvent was added to degreaser B.

TABLE I

DEGREASER A

| (TIME hrs.) | ACID ACCEPTANCE[1] LIQUID | ACID ACCEPTANCE[1] CONDENS. | pH LIQUID | NVM (%)[2] LIQUID | $H_2O$ (ppm) LIQUID | TBA(ppm)[3] LIQUID | MIXED AMYLENES(%) LIQUID | MIXED AMYLENES(%) CONDENS. | PROPYLENE OXIDE(%) LIQUID | PROPYLENE OXIDE(%) CONDENS. | BUTYLENE OXIDE(%) LIQUID | BUTYLENE OXIDE(%) CONDENS. |
|---|---|---|---|---|---|---|---|---|---|---|---|---|
| 0 | 0.24 | — | 8.6 | 0.01 | 38 | 8 | 0.48 | — | 0.30 | — | 0.10 | — |
| 48 | 0.29 | 0.16 | 7.6 | 0.67 | 14 | 9 | 0.30 | Not. Avail. | 0.31 | Not. Avail. | 0.13 | Not Avail. |
| 96* | 0.31 | 0.20 | 6.9 | 3.5 | 20 | 8 | 0.23 | 0.51 | 0.34 | 0.23 | 0.15 | 0.03 |
| 216 | 0.34 | 0.20 | 6.9 | 6.0 | 16 | 9 | 0.20 | 0.46 | 0.38 | 0.26 | 0.16 | 0.05 |
| 264* | 0.34 | 0.20 | 7.5 | 3.3 | 26 | 9 | 0.28 | 0.39 | 0.36 | 0.27 | 0.15 | 0.04 |
| 360 | 0.32 | 0.22 | 7.7 | 2.7 | 30 | 10 | 0.29 | 0.47 | 0.36 | 0.30 | 0.15 | 0.06 |
| 408 | 0.33 | 0.19 | 7.2 | 3.8 | 33 | 11 | 0.21 | 0.47 | 0.38 | 0.26 | 0.16 | 0.05 |
| 456 | 0.36 | 0.20 | 7.4 | 6.8 | 1400 | 17 | 0.17 | 0.38 | 0.46 | 0.30 | 0.23 | 0.06 |
| 576 | 0.39 | Not. Avail. | 6.9 | 10.2 | 1900 | 9 | 0.10 | Not. Avail. | 0.47 | Not. Avail. | 0.26 | Not Avail. |
| 696** | 0.27 | 0.15 | 7.1 | 1.7 | 200 | 3 | 0.33 | 0.75 | 0.36 | 0.23 | 0.14 | 0.05 |
| 744 | 0.29 | 0.16 | 6.8 | 2.9 | 43 | 5 | 0.28 | 0.64 | 0.39 | 0.24 | 0.15 | 0.05 |

*2 gallons of solvent added.
**6 gallons of solvent added.
[1]Expressed as % equivalents of NaOH
[2]Non-volatile matter after filtration
[3]Tertiary butyl amine.

TABLE II

DEGREASER B

| (TIME hrs.) | ACID ACCEPTANCE[1] LIQUID | ACID ACCEPTANCE[1] CONDENS. | pH LIQUID | NVM (%)[2] LIQUID | $H_2O$ (ppm) LIQUID | TBA(ppm)[3] LIQUID | MIXED AMYLENES(%) LIQUID | MIXED AMYLENES(%) CONDENS. | PROPYLENE OXIDE(%) LIQUID | PROPYLENE OXIDE(%) CONDENS. | BUTYLENE OXIDE(%) LIQUID | BUTYLENE OXIDE(%) CONDENS. |
|---|---|---|---|---|---|---|---|---|---|---|---|---|
| 0 | 0.24 | — | 8.6 | 0.01 | 38 | 8 | 0.48 | — | 0.30 | — | 0.10 | — |
| 6 | 0.28 | 0.16 | 8.6 | 0.06 | 42 | 7 | 0.35 | 0.70 | 0.31 | 0.22 | 0.12 | 0.03 |
| 30 | 0.28 | 0.16 | 8.6 | 0.11 | 22 | 9 | 0.29 | 0.62 | 0.35 | 0.22 | 0.16 | 0.03 |
| 147 | 0.36 | 0.19 | 8.3 | 0.67 | 265 | 15 | 0.21 | 0.43 | 0.41 | 0.25 | 0.19 | 0.03 |
| 195 | 0.34 | 0.19 | 8.2 | 0.62 | 76 | 14 | 0.25 | 0.50 | 0.38 | 0.25 | 0.17 | 0.03 |
| 315 | 0.33 | 0.20 | 8.1 | 0.66 | 86 | 15 | 0.28 | 0.54 | 0.37 | 0.24 | 0.16 | 0.04 |
| 411 | 0.35 | 0.20 | 8.1 | 0.96 | 42 | 12 | 0.22 | 0.45 | 0.45 | 0.30 | 0.23 | 0.07 |
| 459 | 0.35 | 0.18 | 8.3 | 0.87 | 37 | 16 | 0.26 | 0.52 | 0.45 | 0.27 | 0.22 | 0.05 |
| 483 | 0.35 | 0.19 | 8.2 | 0.93 | 58 | 15 | 0.25 | 0.51 | 0.46 | 0.29 | 0.23 | 0.06 |
| 631 | 0.37 | 0.21 | 8.3 | 1.3 | 27 | 17 | 0.20 | 0.40 | 0.47 | 0.30 | 0.24 | 0.07 |
| 655 | 0.38 | 0.21 | 8.2 | 1.4 | 38 | 20 | 0.20 | 0.38 | 0.51 | 0.31 | 0.27 | 0.07 |

[1]Expressed as % equivalents of NaOH
[2]Non-volatile matter after filtration
[3]Tertiary butyl amine The test results show that the acid acceptance number, which is the most generally accepted parameter used to characterize the stability of chlorinated solvents, was constant in both the liquid and condensate. The pH of the solvent remained essentially constant. The additives distributed between the phases in accordance with their azeotropic properties and their relative boiling points compared with methylene chloride (BP 40.1° C.). The mixed amylenes (boiling point 38° C.) became more concentrated in the vapor phase. The propylene oxide (BP 35° C.) was almost equally distributed while the butylene oxide (BP 62° C.) was mainly concentrated in the liquid. The tertiary butyl amine (BP 45° C.) was primarily concentrated in the liquid. Since the tertiary butyl amine was originally present at rather low levels (8 ppm), the vapor phase was not analyzed for it except in spot tests.

What is claimed is:

1. A stabilized methylene chloride composition consisting essentially of methylene chloride and mixed amylenes in amounts varying from about 0.01% to about 2.5% by weight, propylene oxide in amounts varying from about 0.01% to about 2% by weight, butylene oxide in amounts varying from about 0.1% to about 0.75% by weight, and tertiary butylamine in amounts varying from about 1 ppm to about 0.01% by weight, of the methylene chloride.

2. The composition of claim 1 wherein said mixed amylenes contain 2-methyl-2-butene, 2-methyl-1-butene and 3-methyl-1-butene.

3. A method for vapor degreasing metals comprising contacting the metals to be degreased with a stabilized methylene chloride composition consisting essentially of methylene chloride and mixed amylenes in amounts varying from about 0.01% to about 2.5% by weight, propylene oxide in amounts varying from about 0.01% to about 2% by weight, butylene oxide in amounts varying from about 0.1% to about 0.75% by weight, and tertiary butylamine in amounts varying from about 1 ppm to about 0.01% by weight, of the methylene chloride.

* * * * *